(12) United States Patent
Evdokimov et al.

(10) Patent No.: US 9,023,102 B2
(45) Date of Patent: May 5, 2015

(54) REIMPLANTABLE HEART VALVE PROSTHESIS

(75) Inventors: Sergey Vasilyevich Evdokimov, Penzenskaya Oblast (RU); Alexandr Sergeyevich Evdokimov, Penzenskaya Oblast (RU); Eduard Yurievich Goncharov, Penza (RU); Alexandr Nikolayevich Filippov, Penza (RU)

(73) Assignee: MedEng, Penza (RU)

( * ) Notice: Subject to any disclaimer, the term of this patent is extended or adjusted under 35 U.S.C. 154(b) by 767 days.

(21) Appl. No.: 12/575,002

(22) Filed: Oct. 7, 2009

(65) Prior Publication Data

US 2010/0241221 A1    Sep. 23, 2010

(30) Foreign Application Priority Data

Mar. 19, 2009    (RU) .................................. 2009110354

(51) Int. Cl.
    *A61F 2/24*    (2006.01)
(52) U.S. Cl.
    CPC .................................... *A61F 2/2403* (2013.01)
(58) Field of Classification Search
    CPC .......................................................... A61F 2/2469
    USPC ................................................. 623/2.38–2.41
    See application file for complete search history.

(56) References Cited

U.S. PATENT DOCUMENTS

| | | | | |
|---|---|---|---|---|
| 3,099,016 A * | 7/1963 | Edwards | .......................... | 623/2.4 |
| 3,464,065 A * | 9/1969 | Cromie | .......................... | 623/2.38 |
| 3,551,913 A * | 1/1971 | Shirley et al. | ................. | 623/2.38 |
| 3,587,115 A | 6/1971 | Shiley | | |
| 3,691,567 A * | 9/1972 | Cromie | ......................... | 623/2.35 |
| 3,997,923 A * | 12/1976 | Possis | .............................. | 623/2.4 |
| 4,086,665 A * | 5/1978 | Poirier | .......................... | 623/1.44 |
| 4,197,593 A * | 4/1980 | Kaster et al. | .................. | 623/2.39 |
| 4,477,930 A * | 10/1984 | Totten et al. | .................. | 623/2.15 |
| 4,680,031 A * | 7/1987 | Alonso | ......................... | 623/2.13 |
| 4,790,843 A | 12/1988 | Carpentier et al. | | |
| 5,137,532 A | 8/1992 | Bokros et al. | | |
| 5,522,885 A * | 6/1996 | Love et al. | .................... | 623/2.11 |
| 5,766,240 A * | 6/1998 | Johnson | ......................... | 623/2.39 |
| 6,176,877 B1 * | 1/2001 | Buchanan et al. | ............ | 623/2.39 |
| 6,893,459 B1 | 5/2005 | Macoviak | | |
| 7,959,674 B2 * | 6/2011 | Shu et al. | ........................ | 623/2.4 |

FOREIGN PATENT DOCUMENTS

| | | |
|---|---|---|
| CA | 2218621 | 10/2006 |
| RU | 2350300 | 3/2009 |

OTHER PUBLICATIONS

European Search Report for EP09173735.3, (Feb. 17, 2010).

* cited by examiner

*Primary Examiner* — Paul Prebilic
(74) *Attorney, Agent, or Firm* — Bachman & LaPointe, P.C.

(57) ABSTRACT

A medical device used in cardiac surgery for replacement of diseased heart valves in humans. A heart valve prosthesis comprising a housing 1 having a projection 3 along its whole perimeter 2, an occluder 4 which restricts the blood backflow (I), and a cuff 5 made of fabric and having a mounting surface 6which comes into contact with cardiac tissues (II), and an outer surface 7 which comes into contact with the blood flow. Inside the cuff 5 are located a stent 8 forming an opening 9 for installation of the prosthesis housing 1, a supporting element 10 and a retaining element 11 which fix the projection 3 of the housing 1 within the stent 8 of the cuff 5 forming a quick-dismountable junction of the housing 1 with the cuff 5.

3 Claims, 2 Drawing Sheets

REIMPLANTABLE HEART VALVE PROSTHESIS

BACKGROUND OF THE INVENTION

The invention relates to medical devices and can be used in cardiac surgery for replacement of the diseased native aortic and mitral heart valves in humans. This invention can also be successfully used for replacement of the diseased tricuspid valve or pulmonary valve.

There is a certain heart valve prosthesis (SU 1761132) comprising an annular housing, a disc occluder pivoting eccentrically within the housing between an open position, which allows the passage of the direct blood flow, and a closed position, which restricts the blood backflow, a cuff fixed between projections located at the housing faces having a mounting surface which comes into contact with the cardiac tissues, an inner surface embracing the housing, and an outer surface which comes into contact with the blood flow. The cuff is made of a woven material and is permanently attached to the housing by means of suture bandage rings.

There is a certain heart valve prosthesis (U.S. Pat. No. 5,137,532) comprising an annular housing, an occluder in the form of two leaflets pivoting eccentrically within the housing between an open position which allows the passage of the direct blood flow, and a closed position which restricts the blood backflow, a cuff permanently attached to the projection located at the outer housing surface by means of bandage rings. The cuff has a mounting surface which comes into contact with the cardiac tissues, an inner surface embracing the housing, and an outer surface which comes into contact with the blood flow.

There is a certain heart valve prosthesis (U.S. Pat. No. 4,477,930) comprising an annular housing, an occluder in the form of three elastic leaflets made of biological material which move between their open and closed positions to allow the passage of the direct blood flow and restrict the blood backflow. The housing is made of elastic polymeric material or metal, which deforms during leaflet closure and compensates loads working on the leaflets. A cuff permanently attached to the outer housing surface by means of sutures has a mounting surface which comes into contact with the cardiac tissues, an inner surface embracing the housing, and an outer surface which comes into contact with the blood flow.

All three the above-mentioned prostheses represent typical models of various heart valve prostheses which are used widely and successfully throughout the world. But all of them have a common shortcoming, that is, that their cuff is permanently attached to the housing and that its attachment is carried out in factory settings. In this connection it is possible to damage the prosthesis during its implantation when suturing the cuff to the fibrous ring. And during reimplantation of the prosthesis it is necessary to remove the prosthesis together with the cuff from the fibrous ring and this is a very traumatic operation requiring additional time for surgery on the non-beating heart. These manipulations increase the risks of operative complications and patient death.

There is a certain heart valve prosthesis (RU Patent Application No. 2007127767, now RU Patent No. 2 350 300) comprising an annular housing having at least one projection along its outer perimeter, an occluder which restricts the blood backflow, and a cuff made of porous material, for example, synthetic fabric, and having a mounting surface which comes into contact with the cardiac tissues and an outer surface which comes into contact with the blood flow. The cuff has a stent forming an opening for installation of the annular housing of the prosthesis, supporting and retaining elements, which fix the projection of the housing within the stent of the cuff forming a quick-dismountable junction of the housing with the cuff.

This heart valve prosthesis, chosen as prototype, provides the possibility to install it easily and safely and, in case of valve dysfunction, the possibility to replace it without removal of its cuff. However, it is possible to modernize this prosthesis in order to increase its safety of use and reliability.

The objective of the proposed invention is to reduce risk of trauma to the patient during reimplantation of the heart valve prosthesis and increase reliability of the implanted prosthesis.

SUMMARY OF THE INVENTION

Proposed is a heart valve prosthesis comprising a housing having at least one projection along its whole outer perimeter, an occluder which restricts the blood backflow, and a cuff made of some porous material, for example, synthetic fabric, and having a mounting surface which comes into contact with the cardiac tissues and an outer surface which comes into contact with the blood flow. Inside the cuff are provided a rigid stent forming an opening for the installation of the annular housing of the prosthesis, supporting and retaining elements which attach the cuff to said housing projection wherein the supporting element in the form of an annular projection upon the stent is located within the zone adjacent to the mounting surface of the cuff, and the retaining element in the form of a ring is located in the zone adjacent to the outer surface of the cuff. Furthermore the retaining element has two cams protruding above the outer surface of the cuff and a cut in the zone between the cams.

The retaining element is made of elastic bioinert material, for example, a titanium or titanium-nickel alloy.

Furthermore, protuberances are provided at the cam surfaces facing each other which form a clearance between themselves sufficient for placement of the instrument's ends, while slots are provided at the opposite cam surfaces.

In addition to this, the retaining element is of varying width, and its minimum width is in the zone between the cams, while its maximum width is in the zone located at the diametrically opposite side of the retaining element.

Proposed also is an instrument for installation of the valve housing into the cuff which is in the form of an anatomically curved distractor with an angle limiter for separation of the distractor's ends, while the holes having bigger size than the counterpart size of the cam protuberances of the retaining element of the heart valve prosthesis are provided at the distractor's ends.

Search revealed no known technical solutions combined with the limitations similar to limitations which distinguish the stated solution from the prototype.

The proposed heart valve prosthesis decreases risk of damage to the prosthesis and risk of trauma to the patient during heart valve replacement and reimplantation of the prosthesis and enhances it reliability.

The placement of the supporting element in the zone adjacent to the mounting surface of the cuff and making it in the form of an annular projection upon the stent ensure the possibility to install the valve housing into the corresponding anatomic position without causing damage to the surrounding cardiac structures.

The placement of the retaining element in the zone adjacent to the outer surface of the cuff and making it in the form of a ring ensure preservation of the form and overall dimensions of the cuff and thus facilitating ease of suturing of the cuff to the fibrous ring of the operated heart valve.

The provision of the retaining element with two cams protruding above the outer surface of the cuff alongside with a cut in the zone between said cams ensures the possibility to change with instrument the internal diameter of the retaining element without causing damage to the cuff.

The provision of the retaining element made of elastic bioinert material, for example, a titanium or titanium-nickel alloy, ensures return and preservation of the initial internal diameter of the retaining element after its expansion during installation of the valve housing into the cuff or removal of the valve housing from the cuff.

The provision of the protuberances at the cam surfaces which face each other and protrude above the outer surface of the cuff with a clearance between themselves sufficient for placement of the instrument's ends ensures the possibility for easy and secure engagement of said protuberances with the instrument which allows to perform a stable and controlled expansion of the retaining element in order to pass the valve housing through it.

The provision of the slots at the opposite surfaces of the cams ensures the possibility to place within them a fixing element, for instance, a suture knot, in order to prevent a spontaneous change of the internal diameter of the ring, thus increasing the reliability of the heart valve prosthesis.

The provision of the varying width of the retaining element, with its minimum in the zone between the cams and its maximum in the zone located at the diametrically opposite side of the retaining element, ensures the preservation of its circular form during its expansion and that facilitates the passage of the annular projection of the valve housing through it.

The provision of the instrument for installation of the valve housing into the cuff in the form of an anatomically curved distractor ensures an easy and safe expansion of the retaining element by means of the usual surgical instrument.

The provision of the distractor with an angle limiter for separation of the distractor's ends ensures the sufficient degree of the expansion of the retaining element within the limits of elastic strain to permit the passage of the valve housing and restrict further enlargement of the internal diameter of the retaining element.

The provision of the distractor's ends with the holes sized somewhat bigger than the size of the protuberances of the cams of the retaining element ensures a secure engagement of the cams with the distractor's ends and their separation in order to expand the retaining element.

BRIEF DESCRIPTION OF THE DRAWINGS

The invention is described by means of the following drawings, wherein.

DETAILED DESCRIPTION

For convenience the direction of the blood backflow is shown by the arrow (I), while the heart surface which comes into contact with the mounting surface of the cuff is shown by (II).

Figure 2:
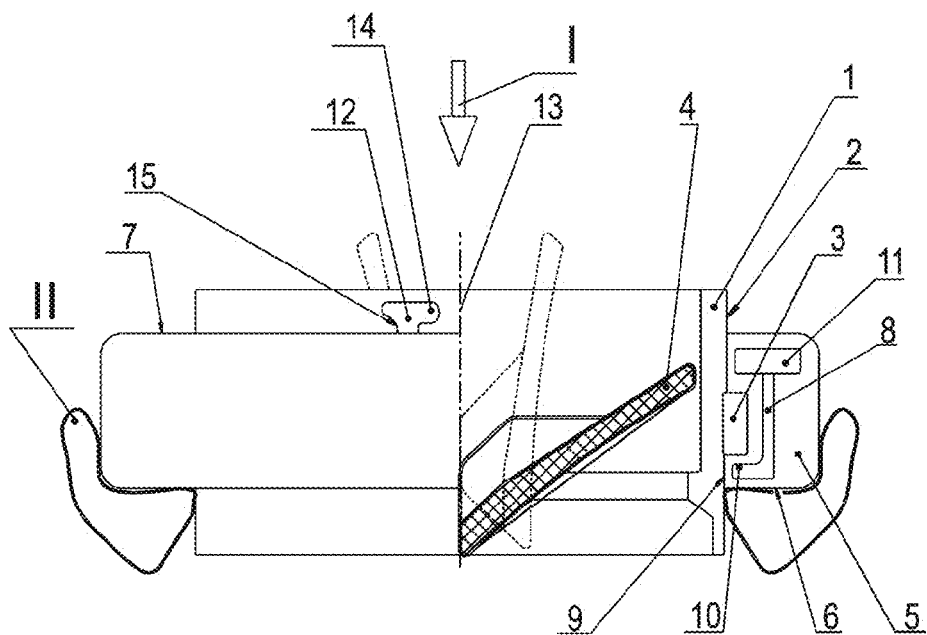
FIG. 2 is a diametral section of the heart valve prosthesis.

A heart valve prosthesis (FIG. 2) comprising a housing 1 having a projection 3 along its whole perimeter 2, an occluder 4 which restricts the blood backflow (I), and a cuff 5 made of fabric and having a mounting surface 6 which comes into contact with the cardiac tissues (II), and an outer surface 7 which comes into contact with the blood flow.

Inside the cuff 5 are located a stent 8 forming an opening 9 for installation of the prosthesis housing 1, a supporting element 10 and a retaining element 11 which fix the projection 3 of the housing 1 within the stent 8 of the cuff 5 forming a quick-dismountable junction of the housing 1 with the cuff 5.

The retaining element 11 in the form of a ring has two cams 12 protruding above the outer surface 7 of the cuff 5 with a cut 13 in the zone between the cams 12.

Figure 3:
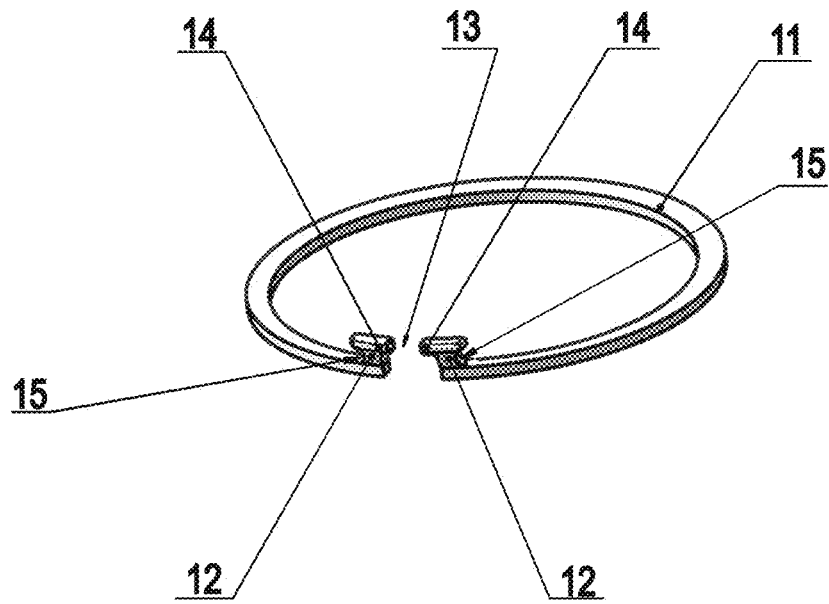
FIG. 3 is a perspective view of the retaining element.
Figure 4:
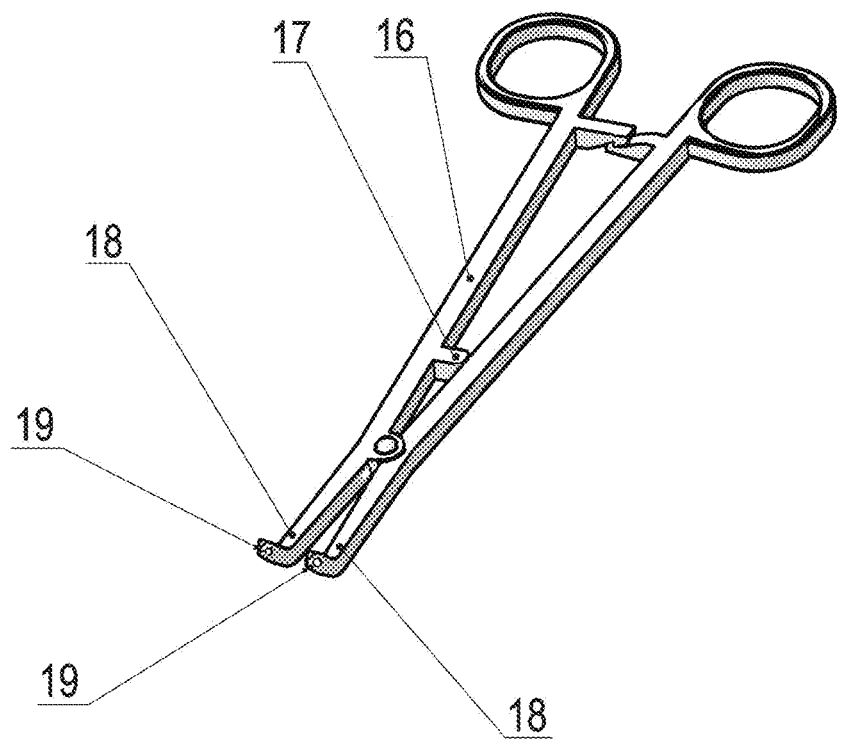
FIG. 4 is a perspective view of the instrument for installation of the heart valve prosthesis.

Protuberances 14 which oppose each other with a clearance are provided at the surfaces of the cams 12 (FIG. 3) and they protrude above the outer surface 7 of the cuff 5, while slots 15 are provided at the opposite surfaces of the cams 12.

An instrument for installation of the valve housing 1 into the cuff 5 is provided in the form of an anatomically curved distractor 16 with an angle limiter 17 for separation of the distractor's ends 18, while the holes 19 are provided at the distractor's ends 18.

Figure 1:
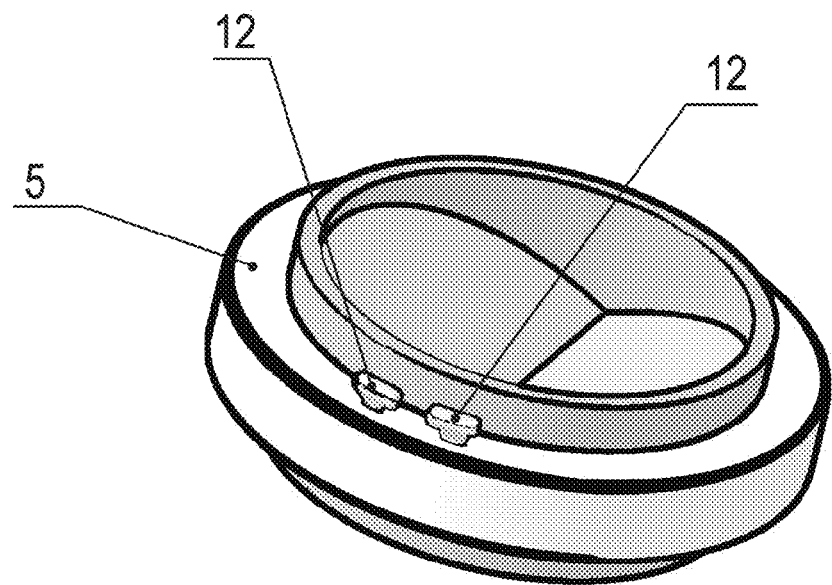
FIG. 1 is a perspective view of the reimplantable aortic bileaflet mechanical heart valve prosthesis.

The heart valve prosthesis illustrated in FIG. 1 functions as follows.

The cuff 5 placed on its mounting surface 6 is sutured to the fibrous ring II of the operated heart valve using standard surgical procedures common for heart valve replacements. The supporting element 10 upon the stent 8 and the retaining element 11 form an annular socket with diameter equal to the outer diameter of the housing 1, and the inner surface of the stent 8 forms an annular recess inside the socket with diameter and width which correspond to the diameter and width of the projection 3 located along the outer perimeter 2 of the housing 1 of the heart valve prosthesis.

Then the ends 18 of the distractor 16 are placed into the clearance between the protuberances 14 in order to engage them with the holes 19 provided at the ends 18 of the distractor 16. This prevents the slippage of the ends 18 from the protuberances 14 during further manipulations. After that the ends 18 of the distractor 16 are separated in order to expand the retaining element 11 until its inner diameter becomes a bit bigger than the outer diameter of the projection 3 of the housing 1. The degree of separation of the ends 18 of the distractor 16 is restricted by the limiter 17.

After this the housing 1 is inserted into the stent 8 till interaction with the supporting element 10 of the stent 8. Then the ends 18 of the distractor 16 are joined in order to release the cams 12. Alongside this the retaining element 11, due to elastic properties of its material, returns to its initial state and fixes the projection 3 inside the cuff 5 between the supporting element 10 and the retaining element 11. In order to prevent a spontaneous expansion of the retaining element 11 surgeon ties the cams 12 up with a suture by placing it into the slots 15 of the cams 12.

In case of dysfunction of the prosthesis or when it is necessary to replace it with a bioprosthesis or other model of the heart valve prosthesis, surgeon performs standard preparatory surgical procedures required for reimplantation of the heart valve prosthesis. Alongside this the cuff 5 is not removed from the cardiac tissues.

Then surgeon cuts and removes the suture from the slots 15 in order to release the cams 12. After that the ends 18 of the distractor 16 are placed into the clearance between the protuberances 14 in order to engage them with the holes 19 provided at the ends 18 of the distractor 16. Then the ends 18 of the distractor 16 are separated in order to expand the retaining element 11 until its inner diameter becomes a bit bigger than the outer diameter of the projection 3 of the housing 1. The degree of separation of the ends 18 of the distractor 16 is restricted by the limiter 17. After this the housing 1 of the heart valve prosthesis is removed from the cuff 5 and the housing 1 of the other heart valve prosthesis is installed into the cuff 4 in accordance with the above-mentioned procedure.

The proposed heart valve prosthesis, while preserving all advantages of the prototype, ensures a decrease of risks of trauma to the intracardiac structures of the patient during heart valve replacement and reimplantation of the heart valve and also enhances its reliability.

The invention claimed is:

1. A heart valve prosthesis comprising an annular housing having an outer perimeter and at least one projection along the outer perimeter, an occluder which restricts blood backflow, and a cuff made of a porous material, the cuff having a mounting surface which is configured to come into contact with cardiac tissue and an outer surface which comes into contact with blood flow, the cuff has an inside provided with a rigid stent forming an opening for installation of the annular housing of the prosthesis, and a supporting element and a retaining element which attach the cuff to said at least one projection, the supporting element comprises an annular projection on the stent located within a zone adjacent to the mounting surface of the cuff, and the retaining element comprises a ring defining an inner diameter and having two cams protruding above the outer surface of the cuff and a cut fully splitting the retaining element in a zone between the cams, wherein the inner diameter of the ring can become bigger and wherein the retaining element is located in the zone adjacent to the outer surface of the cuff, wherein the retaining element is configured to form a quick-dismountable junction of the annular housing with the cuff, and the retaining element is of varying width, and its minimum width is in the zone between the cams, while its maximum width is in the zone located at the diametrically opposite side of the retaining element for ensuring the preservation of a circular form of the retaining element during its expansion and facilitating the passage of the annular projection of the valve housing through it, and wherein slots are provided at opposite surfaces of the cams to place within them a fixing element in order to prevent a spontaneous change of the internal diameter of the retaining element.

2. A heart valve prosthesis according to claim 1 wherein the retaining element is made of elastic bioinert material.

3. A heart valve prosthesis according to claim 1 wherein protuberances are provided at the cam surfaces facing each other and defining the cut which forms a clearance sufficient for placement of an instrument's ends, and slots are provided at the cams.

* * * * *